US006436700B1

(12) United States Patent
Roth et al.

(10) Patent No.: US 6,436,700 B1
(45) Date of Patent: Aug. 20, 2002

(54) ANTI-SENSE P21 K-RAS (75) Inventors: Jack A. Roth; Tapas Mukopadhyay; Michael Tainsky, all of Houston, TX (US)

(73) Assignee: Board of Regents, The University of Texas Systems, Austin, TX (US)

( * ) Notice: Subject to any disclaimer, the term of this patent is extended or adjusted under 35 U.S.C. 154(b) by 0 days.

(21) Appl. No.: 07/987,235

(22) Filed: Dec. 7, 1992

Related U.S. Application Data (63) Continuation of application No. 07/665,538, filed on Mar. 6, 1991, now abandoned.

(51) Int. Cl.⁷ .......................... C12N 15/00; C07H 21/04
(52) U.S. Cl. ................................ 435/320.1; 536/24.5
(58) Field of Search .......................... 435/172.3, 320.1; 536/23.1, 24.5

(56) References Cited

U.S. PATENT DOCUMENTS 4,740,463 A * 4/1988 Weinberg

FOREIGN PATENT DOCUMENTS

| FR | 2688514 | 9/1993 |
|---|---|---|
| WO | WO 90/10448 | 9/1990 |
| WO | WO 93/03769 | 3/1993 |
| WO | WO 94/10323 | 5/1994 |
| WO | WO 94/24297 | 10/1994 |
| WO | WO 95/02697 | 1/1995 |

OTHER PUBLICATIONS

Izant et al. (1984) Cell 36, 1007–1015.*
Izant et al. (1984) "Inhibition of Thymidine Kinase Gene Expression by Anti–sense RNA . . . " Cell 36, 1007–1015.*
Hwang et al (1984) Molec. Cell Biol. 4, 2289–2297.*
Casey et al., "Growth Suppression of Human Breast Cancer Cells by the Introduction of a Wild–Type p53 Gene," *Oncogene*, 6:1791–1797, 1991.
Wills and Menzel, "Adenovirus Vectors for Gene Therapy of Cancer," *Journal of Cellular Biochemistry*, p. 204, Abstract #S216, Mar.–Apr. 1993.
Zhang et al., "Generation and Identification of Recombinant Adenovirus by Liposome–Mediated Transfection and PCR Analysis," *BioTechniques*, 15(5):868–872, 1993.
Gunning, Peter, et al., "A human β–actin expression vector system directs high–level accumulation of antisense transcripts", *Proc. Natl. Acad. Sci. USA*, 84:4831–4835 (1987).

Mercola, Dan, et al., "Antisense RNA: Eukaryotic Controls", *Gene*, 72:253–265 (1988).
Munroe, Stephen H., "Antisense RNA inhibits splicing of pre–mRNA in vitro", *The EMBO Journal*, 7(8):2523–2532 (1988).
Magrath, Ian, "Tumor–specific antisense oligonucleotides for controlling cancer", Abstract No. 114:55778n, *Chemical Abstracts*, 114(7):68 (1991).
International Search Report (mailed Aug. 20, 1992).
Wahran et al., Tumour Biol, 6:41–56, 1985.
Taya et al., EMBO J., 3:2943–2946, 1984.
Finkel et al., Cell, 37:151–158, 1984.
Feig et al., Science, 223:698–701, 1984.
Santos et al., Science, 223:661–664, 1984.
Shimizu et al., Nature, 304:497–500, 1983.
McGrath et al., Nature, 304:501–506, 1983.
Miller et al., BioTechniques, 7(9):980–990, 1989.
Mukhopadhyay et al., Cancer Res, 51:1744–1748, 1991.
Debus et al., J Cancer Res Clin Oncol, 116(Suppl Part 1):5–162, Abstract # A2.037.09, 1990.
Khokha et al., Science, 243:957–950, 1989.
Kasid et al., Science, 243:1354–1356, 1989.
Delauney et al., PNAS, 85: 4300–4304, 1988.
Prochownik et al., Mol Cell Biol, 8(9):3683–3695, 1988.
Griep & Westphal, PNAS, 85:6806–6810, 1988.
Vogelstein et al., N Engl J Med, 319(9):525–532, 1988.
Stowers et al., Cancer Res, 47:3212–3219, 1987.
Winter & Perucho, Mol Cell Biol, 6:2562–2570, 1986.
Toftgard et al., Carcinogenesis, 6(4):655–657, 1985.
Kris et al., Int J Cancer, 35:227–230, 1985.
Johnson et al., J Exp Med, 162:1732–1737, 1985.

* cited by examiner

*Primary Examiner*—Deborah Crouch
(74) *Attorney, Agent, or Firm*—Fulbright & Jaworski, LLP (57) ABSTRACT

Disclosed are methods and compositions for the selective inhibition gene expression through the application of antisense RNA technology. Antisense RNA constructs of the present invention employ the use of antisense intron DNA corresponding to distinct intron regions of the gene whose expression is targeted for down-regulation. In an exemplary embodiment, a human lung cancer cell line (NCI-H460a) with a homozygous spontaneous K-ras mutation was transfected with a recombinant plasmid that synthesizes a genomic segment of K-ras in antisense orientation. Translation of the mutated K-ras mRNA was specifically inhibited, whereas expression of H-ras and N-ras was unchanged. A three-fold growth inhibition occurred in H460a cells when expression of the mutated ras p21 protein was down-regulated by antisense RNA and cells remained viable. The growth of H460a tumors in nu/nu mice was substantially reduced by expressed K-ras antisense RNA.

7 Claims, 6 Drawing Sheets

ANTI-SENSE P21 K-RAS

This application is a continuation of application Ser. No. 07/665,538, filed Mar. 6, 1991, now abandoned.

The government may own certain rights in the present invention pursuant to NIH grant CA 45187.

BACKGROUND OF THE INVENTION

1. Field of the Invention

The present invention relates to methods and nucleic acid compositions for selectively inhibiting gene expressing, involving the preparation and use of anti-sense RNA molecules that encode sequences complementary to distinct intron regions for the inhibition of, for example, oncogene expression.

2. Description of the Related Art

It is now well established that a variety of diseases, ranging from certain cancers to various genetic defects, are caused, at least in part, by genetic abnormalities that result in either the over expression of one or more genes, or the expression of an abnormal or mutant gene or genes. For example, many forms of cancer in man are now known to be the result of, at least indirectly, the expression of "oncogenes". Oncogenes are genetically altered genes whose altered expression product somehow disrupts normal cellular function or control (Spandidos, et al., 1989).

Most oncogenes studied to date have been found to be "activated" as the result of a mutation, often a point mutation, in the coding region of a normal cellular gene or of a "protooncogene", that results in amino acid substitutions in the protein expression product. This altered expression product, in turn, exhibits an abnormal biological function that somehow takes part in the neoplastic process (Travali, et al., 1990). The underlying mutations can arise by various means, such as by chemical mutagenesis or ionizing radiation.

A number of oncogenes have now been identified and characterized to varying degrees, including ras, myc, neu, rat, erb, src, Fms, jun and abl (Travali, et al., 1990; Minna, 1989; Bishop, 1987). It is quite likely that as our knowledge of tumorigenesis increases, additional oncogenes will be identified and characterized. Many of the foregoing, including ras, myc and erbB, comprise families of genes, whose expression product bear sequence similarities to other members of the family (Shih, et al., 1984; Bos, 1989; Schwab, et al., 1985). In the case of many of these gene families, it is typical that oncogenesis involves an activation of only one member of the family, with other "unactivated" members serving a role in normal cellular functions (Id.).

The study of DNA-mediated gene transfer has revealed the existence of activated cellular oncogenes in a variety of human tumors (for review, see Cooper, et al., 1982). Oncogenes have been identified in human bladder, colon, lung and mammary carcinoma cell lines (Krontiris, et al., 1981; Murray, et al., 1981; Perucho, et al., 1981), promyelocytic leukemia (Murray, et al., 1981), neuroblastoma (Shimizu, et al., 1983) and sarcoma cell lines (Pulciani, et al., 1982), and various solid tumors including carcinomas of the lung, and pancreas (Pulciani, et al., 1982). Studies have demonstrated that various transforming genes detected by transfection correspond to activated cellular homologues of retroviral oncogenes (Pulciani, et al., 1982; Der, et al., 1982; Parada, et al., 1982; Santos, et al., 1982), although others have no known retroviral cognate (Tulciani, et al., 1982; Lane, et al., 1982).

The ras oncogene family has been perhaps the best characterized to date (Barbacid, 1987; Bos, 1989). Most of the identified transforming genes in human carcinomas have been a member of the ras gene family, which encode immunologically related proteins having a molecular weight of 21,000 (p21) (Ellis, et al., 1981; Papageorge, et al., 1982). This family is comprised of at least 3 members, one transduces as H-ras in the Harvey strain of murine sarcoma virus (Ellis, et al., 1981), one as K-ras and Kirsten murine sarcoma virus (Ellis, et al., 1981), and one identified by low stringency hybridization to H-ras, termed N-ras (Shimizu, et al., 1983). As noted, all members of the ras gene family encode closely related proteins of approximately 21,000 Daltons which have been designated p21s (Ellis, et al, 1981). The level of p21 expression is similar in many different human tumor cells, independent of whether the cell contains an activated ras gene detectable by transfection.

Nucleotide sequence analysis of the H-ras transforming gene of the EJ human bladder carcinoma has indicated that the transforming activity of this gene is a consequence of a point mutation altering amino acid 12 of p21 from glycine to valine (Tabin, et al., 1982). Studies of proteins encoded by K-ras genes activated in four human lung and colon carcinoma cell lines indicated that the transforming activity of K-ras in these human tumors was also a consequence of structural mutations (Der and Cooper, 1983). Other mutations have been found to result in ras gene activation as well. For example, the H-ras gene activated in a lung carcinoma cell line encodes the normal amino acid position 12 but is mutated at codon 61 to encode leucine rather than glutamine (Yuasa, et al., 1983). An N-ras gene activated in a human neural blastoma cell line is also mutated at codon 61 but encodes lysine rather that glutamine (Taparowski, et al., 1983). Thus, studies such as these have indicated that ras genes in human neoplasms are commonly activated by structural mutations, often point mutations, that thus far occur at codon 12 or 61 with different amino acid substitutions resulting in ras gene activation in different tumors.

Antisense RNA technology has been developed as an approach to inhibiting gene expression, particularly oncogene expression. An "antisense" RNA molecule is one which contains the complement of, and can therefore hybridize with, protein-encoding RNAs of the cell. It is believed that the hybridization of antisense RNA to its cellular RNA complement can prevent expression of the cellular RNA, perhaps by limiting its translatability. While various studies have involved the processing of RNA or direct introduction of antisense RNA oligonucleotides to cells for the inhibition of gene expression (Brown, et al., 1989; Wickstrom, et al., 1988; Smith, et al., 1986; Buvoli, et al., 1987), the more common means of cellular introduction of antisense RNAs has been through the construction of recombinant vectors which will express antisense RNA once the vector is introduced into the cell.

A principle application of antisense RNA technology has been in connection with attempts to affect the expression of specific genes. For example, Delauney, et al. have reported the use antisense transcripts to inhibit gene expression in transgenic plants (Delauney, et al., 1988). These authors report the down-regulation of chloramphenicol acetyl transferase activity in tobacco plants transformed with CAT sequences through the application of antisense technology.

Antisense technology has also been applied in attempts to inhibit the expression of various oncogenes. For example, Kasid, et al., 1989, report the preparation of recombinant vector construct employing Craf-1 cDNA fragments in an antisense orientation, brought under the control of an adenovirus 2 late promoter. These authors report that the introduction of this recombinant construct into a human squamous carcinoma resulted in a greatly reduced tumorigenic potential relative to cells transfected with control sense transfectants. Similarly, Prochownik, et al., 1988, have reported the use of Cmyc antisense constructs to accelerate differentiation and inhibit $G_1$ progression in Friend Murine Erythroleukemia cells. In contrast, Khokha, et al., 1989, discloses the use of antisense RNAs to confer oncogenicity on 3T3 cells, through the use of antisense RNA to reduce murine tissue inhibitor or metalloproteinases levels.

Unfortunately, the use of current antisense technology often results in failure, particularly where one seeks to selectively inhibit a member of a gene family. This is presumably due to the similarity in underlying DNA sequence, which results in the cross-hybridization of antisense RNA, which retards the expression of genes required for normal cellular functions. An example is presented by Debus, et al., 1990, who reported that in the case of ras oncogenes, antisense ras oligonucleotides kill both normal and cancer cells, which, of course, is not a desired effect.

Therefore, while it is clear that antisense technology shows potential promise as a means of external control of gene expression, it is equally clear that it does suffer particular draw backs, such as in its lack of selectivity where gene families are concerned. There is a particular need, therefore, for a general approach to the design of antisense RNA which will allow selective inhibition of gene expression, even in the case of closely related genes.

SUMMARY OF THE INVENTION

The present invention, in a general and overall sense, addresses one or more of the foregoing or other shortcomings in the prior art by providing a novel approach to the design of antisense RNA molecules, and their coding sequences, in a manner which allows their use to inhibit the expression of specific genes. The inventors believe that the approach offered by the present invention offers more specificity and selectivity than previous approaches. Additionally, it is proposed that the present invention will allow that the development of antisense technology having a much improved ability to inhibit specific gene expression, particularly in those instances where one desires to selectively inhibit a particular gene over that of closely related genes or other members of a gene family.

A principle feature of the present invention is the antisense RNA molecules themselves, which include a region that is complementary to and is capable of hybridizing with an intron region of the gene whose expression is to be inhibited. The inclusion of intron-complementary regions in the antisense RNA constructs of the present invention is believed to be the key to both an improved inhibitory capability as well as selectivity. By way of theory, it is proposed that the use of antisense intron regions provides an improved capability for at least two reasons. It is known that the structure of intron RNA plays a role in RNA processing.

The inventors propose that antisense introns bind to "sense" intron regions found on the initial RNA transcript of the gene, an affects proper RNA processing. Thus, subsequent translation of protein-coding RNAs into their corresponding proteins is retarded or prevented. The use of antisense introns are believed to provide selectivity of inhibition because the exon or "amino acid encoding" region of RNAs coding for closely related proteins are often themselves closely related. This may not be the case for the introns of closely related genes. Thus, where intron regions between two genes are distinct, antisense introns can be designed which will hybridize selectively to a selected gene family member, and not to other family members, and thereby inhibit selectivity.

As used herein, the term "intron" is intended to refer to gene regions that are transcribed into RNA molecules, but processed out of the RNA before the RNA is translated into a protein. In contrast, "exon" regions of genes are those regions which are transcribed into RNA and subsequently translated into proteins.

Thus, where one seeks to selectively inhibit a particular gene or genes over a related gene or genes, the inventors propose the preparation and use of antisense RNA molecules which encode an intron region or regions of the gene which one desires to inhibit selectively, that is distinct from intron regions of genes which one desires to leave unaffected. A "distinct" intron region, as used herein, is intended to refer to an intron region that is sufficiently different from an intron region of another gene such that no cross hybridization would occur under physiologic conditions. Typically, where one intron exhibits a sequence homology of no more than 20% with respect to a second intron, one would not expect hybridization to occur between antisense and sense introns under physiologic conditions.

While it is generally preferred that antisense introns be prepared to be complementary to an entire intron of the gene to be inhibited, it is believed that shorter regions of complementarity can be employed, so long as the antisense construct can be shown in vitro to inhibit expression of the targeted expression product. The inventors believe that the most important intron regions in terms of the preparation of antisense introns will be those regions closest to intron/exon junctions. This is the region where RNA processing takes place. Thus, it is proposed that one will desire to include it in the antisense intron sufficient complementarity with regions within 50–100 nucleotides of the intron/exon junction.

The inventors have found that some antisense exon sequences of the targeted gene can also be included in the antisense constructs of the present invention, so long as the resultant construct maintains its selectivity, and will not seriously inhibit genes whose continued function is relied upon by the cell for normal cellular activities. The amount of antisense exon sequence included within the antisense construct which can be tolerated will likely vary, depending on the particular application envisioned. For example, antisense constructs for down-regulation of K-ras expression have been prepared which include sequences complementary to exons II and III and all of intron II of the K-ras gene. These constructs contain antisense sequences to intron II of K-ras, and selectively inhibit K-ras expression relative to H-ras or N-ras. Thus, in this instance, the inclusion of sequences complementary to exons II and III of K-ras apparently did not result in the significant inhibition of the H-ras or N-ras genes, even though a 300 nucleotide region of complementarity existed with exons of the unaffected genes.

One can readily test whether too much antisense exon DNA has been included in antisense intron constructs of the present invention by simply testing the constructs in vitro to determine whether normal cellular function is affected or whether the expression of related genes having complementary sequences are affected.

It is proposed that the antisense constructs of the present invention, whether they be the antisense RNA molecules (i.e., oligonucleotides) or nucleic acid molecules which encode for antisense RNA molecules, will have their principal application in connection with the down-regulation of oncogene expression. The most preferred oncogenes for application of the present invention will be those which exist as a family of genes, where one desires to selectively inhibit one member of a family over other members. In this regard, one may mention by way of example, the ras, myc, erb or jun families of oncogenes. Certain of these, such as the ras family, involves the activation of protooncogenes by a point mutation, which apparently results in the expression of a biologically abnormal product.

The present invention contemplates that antisense intron RNA can either be applied directly to cells, in the form of oligo-nucleotides incorporating antisense intron sequences, or by introducing into the cell nucleic acid sequences that will encode the desired antisense construct. In the former case, it has been shown by others that antisense oligonucleotides can successfully traverse cellular membranes. The present inventors envision that such an approach may be an option to therapy, particularly where the antisense oligonucleotides are successfully packaged to maintain their stability in circulation, for example, by liposome encapsulation.

Other techniques for direct insertion in the cells include, by way of example, electroporation, or calcium phosphate trans-fection. Furthermore, where one desires to treat conditions of the bone marrow, bone marrow cells can be successfully removed from the body, treated with antisense constructs, and replaced into the body similar to the adoptive immunotherapy approach employed in IL-2 treatment.

It is proposed that a more preferred approach will involve the preparation of vectors which incorporate nucleic acid sequences capable of encoding the desired antisense intron construct, once introduced into the cells to be treated, preferably, these sequences are stably integrated into the genome of the cell. One example of such of vector construct would be a replication defective retrovirus, such as LNSX, LN or N2A, that is made infective by appropriate packaging, such as by GPtenvAM-12 cells. Although the retrovirus would inhibit the growth of the tumor, the expression of the antisense construct in non-tumor cells would be essentially harmless where one prepares a retrovirus construct which encode distinct antisense intron RNA in accordance with the present invention. In addition to retroviruses, it is contemplated that other vectors can be employed, including adenovirus, adeno-associated virus, or vaccinia viruses (Hermonat, et al., 1984; Karlsson, et al., 1985; Mason, et al., 1990).

Therefore, in certain aspects, the present invention contemplates the preparation of nucleic acid molecules which comprise a coding region capable of expressing an antisense "intron" RNA molecule having regions complementary to and capable of hybridizing with an intron region of selected gene. Generally speaking, preferred nucleic acid molecules will be DNA sequences arranged in a vector, such as a virus or plasmid, and positioned under the control of an appropriate promoter. However, antisense RNA can be itself an RNA molecule, such as retrovirus RNA into which the appropriate coding sequences have been incorporated. In either case, the nucleic acid encoding sequences will be arranged in a vector that will preferably be capable of stably integrating the antisense coding sequences into the genome of the targeted cell.

The particular promoter that is employed to control the expression of the antisense RNA in a vector construct is not believed to be particularly crucial, so long as it is capable of expressing the antisense intron RNA in the targeted cell of a rate greater than 5 fold that of the gene to be inhibited.

Thus, where a human cell is targeted, it will be preferred to position the antisense RNA coding region adjacent to and under the control of a promoter that is capable of being expressed in a human cell. Generally speaking, such a promoter might include either a human cellular or viral promoter. By way of example, one may mention the RSV, N2A, LN, LNWC, LNSN, SV40, LNCX or β-actin promoter (Miller, et al., 1989; Hamtzoponlos, et al., 1989).

The most preferred promoters will be those that are capable of being expressed in a wide variety of histologic cell types, and which is capable of continuously expressing the antisense RNA. A preferred example is the β-actin promoter, because the promoter functions effectively in human epithelial cells. Other examples of promoters having a similar capability include RSV and SV40.

In further aspects, the present invention concerns a method of selectively inhibiting the expression of a gene product of a selected gene in a cell, which includes preparing an antisense RNA molecule having a region that is complementary to and capable of hybridizing with a distinct intron region of the selected gene, followed by introducing the antisense RNA into the cell in an amount effective to inhibit the expression of the gene product.

In still further embodiments, the invention concerns a method for the inhibition of tumorigenicity of ras-transformed cells, which includes a first step of testing the cell to identify the particular ras gene that has been activated, preparing an antisense RNA molecule which includes a distinct intron of the activated ras oncogene that is not found in an intron of ras genes which are not activated in the cell, and introducing the antisense RNA into the cell in amounts effective to selectively inhibit the activated ras gene. The inventors have found that the invention has particular applicability to control of ras gene expression, particularly K-ras, and have shown that the expression of a particular ras gene can be effectively inhibited, without affecting cell viability.

In still further embodiments, the present invention relates to methods of preparing genetic constructs for the expressing of antisense intron DNA, which includes incorporation of genomic DNA fragments, as opposed to cDNA, into appropriate vectors for subsequent intracellular incorporation. Of course, the use of cDNAs alone in the preparation of antisense RNA will not be in accordance with the present invention, in that, by definition, cDNAs will not include the required intron sequences. However, intron sequences will be represented in genomic DNA, which therefore provides a useful source of DNA fragments for application to the present invention.

BRIEF DESCRIPTION OF THE DRAWINGS

B) A 2 kb genomic DNA segment from the K-ras oncogene was subcloned into in Apr-1-neo vector in both a sense and antisense orientation. A 2 kb Eco RI/Pst I fragment containing second and third exon sequences together with adjoining flanking intron sequences was isolated from the SP6 vector (Oncogene Sciences) and Klenow enzyme was used to make blunt ends. Apr-1-neo vector was digested with Bam HI and blunt end ligation was performed to obtain the Apr-1-neo AS or Apr-1-neo S constructs.

C) A southern blot analysis of the K-ras oncogene in H460a and H460a transfectants. Blots were probed with P32 nick translated 2 kb Eco R1/Pst1 insert DNA. 1) H460a, (2,3) H460a transfected with Apr-1-neo S $C_1$#1 and $C_2$#1 (4,5) H460a cells transfected with Apr-1-neo AS, $C_3$#32 and $C_2$#32, respectively.

D) A northern blot analysis of sense and antisense K-ras RNA. 1)H460a, (2,3) Apr-1-neo S transfectants, (4,5) Apr-1-neo AS transfected clones.

E,F) A Western blot analysis of K-ras specific p21-protein (1E) and total ras protein (1F) was performed using either pan ras or K-ras specific monoclonal antibodies. 1) Calu-1 control cell line over expressing K-ras specific protein. 2) H460a; 3) H460a Apr-1-neo S; 4,5 ) H460a Apr-1-neo AS.

G) Map of plasmid pH β APr-1-neo

FIG. 2 A) Schematic diagram of K-ras RNA synthesis. A segment of ras cDNA was amplified using oligonucleotide primers corresponding to the 5' region of first exon and 31' of second exon (indicated by arrows) for RNA PCR analysis.

B) An RNA PCR analysis was done to compare the level of K-ras message in H460a and H460a transfectants. As a control, a portion of p53 gene was co-amplified with p53 specific primer which served as an internal control.

C,D) H-ras and N-ras specific amplimers were used to quantitate H-ras/N-ras RNA in the transfectants and parental cell lines. p53 gene amplification is shown as an internal control.

FIG. 3 (A) In vitro growth curve. Cells were seeded at $10^4$ cells/plate and grown for a seven day period. Cells were harvested and counted in a hemocytometer at 24 h intervals. Growth curves for H460A and H460A cells transfected with Apr-1-neo S vector do not show any significant difference, but H460A transfectants carrying Apr-1-neo-AS showed growth inhibition (FIG. 3B). Female BALB/C nu/nu mice were injected with $10^6$ H460a cells subcutaneously in the left flank. Cross-sectional diameters of the external tumor were measured without knowledge of the cell group. Tumor volume was calculated by assuming a spherical shape with the average tumor diameter calculated as the square root of the product of cross-sectional diameters. Palpable tumors were first detected on day 15. Each point represents the mean±SE. C3#32-AS (n=5), C3#1-S (n=5), H460a (n=3). C3#32-AS was compared to C3#1-S or H460a on days 20, 25, 30, 35 ($p<0.05$ by Wilcoxon's Test).

DETAILED DESCRIPTION OF THE PREFERRED EMBODIMENTS

The present invention relates generally to techniques for down-regulating the expression of selected genes, particularly those which contribute to the development or progression of cancers, through the preparation and use of antisense constructs which incorporated the regions that are complementary to distinct intron regions of the gene to be down-regulated. It is believed that the present invention will be generally applicable to the down-regulation of any gene which comprises a distinct intron region. However, it is proposed that the invention will find particular application in the down-regulation of oncogene expression, particularly those oncogenes that are activated through mutation of coding sequences, and even more particularly, to those oncogenes which are members of family wherein one desires to leave unaltered the expression of other family members.

For this and other reasons, the present invention will have particular application to the selective inhibition of ras gene expression. For example, in the case of ras gene tumorigenesis, only one of the various ras gene family members undergoes mutation-based protooncogene activation. The remaining, non-activated ras gene family member (s) serve useful cellular biological functions and are apparently required for normal cellular function. Thus, it is desirable to specifically down-regulate the activated ras gene product, while leaving essentially unaffected, the non-activated ras gene counterparts. Thus, the present invention will have a particular application in the context of preferentially controlling ras gene expressing.

While the present invention is exemplified in terms of the control of ras gene expression, there is, of course, no reason why the present invention will not be similarly applicable to other genes and gene families, in light of the disclosure herein and the general knowledge and skill in the art.

Generally speaking, to practice the present invention in the context of the ras gene system it will be first important to determine which of the various ras genes is involved in the oncogenic process to be retarded. This is a fairly straight-forward undertaking, and involves generally that one first obtain cells which are expressing the activated ras gene product. To determine the nature of the activation, one then simply extracts DNA, amplifies the specific sequences of interest (see Table I below), and shows the presence or absence of the mutation by specific hybridization with a known oligonucleotide sequence.

After the particular activated ras gene has been identified, an appropriate intron region is then selected for constructing the antisense construct. The most appropriate introns are those which have little or no homology to other known genes. In general, it will be preferable to identify an appropriate intron structure for use in connection with the present invention an analysis of the nucleic sequence of the intron, and comparison with selected that of introns of other family members or related genes. The best choice of introns will be those having 1) a different length from corresponding introns and similar location in other members of the gene family, and 2) little or no sequence homology with the introns of the other members.

An alternative, and sometimes simpler method to identify distinct introns involves a comparison of sequence homologies can be ascertained by cross-hybridization of introns from one family member with those of other genes.

In any event, representative methods for cloning ras genes corresponding to the N-ras, K-ras and H-ras genes, have been described in the literature (McGrath, et al., 1983; Shimizu, et al., 1983; Yamamoto, et al., 1985; Kraus, et al., 1984). These teachings should provide those of skill in the art with adequate direction where one seeks to obtain sequences corresponding to the various ras gene intron.

A preferred method for cloning intron sequences is through the application of PCR-amplified cloning. In this relatively well known technique, one employs oligonucleotide primers which allow the specific amplification of the desired intron region. The primer itself corresponds to exon sequences, in that these sequences will most likely be generally available in the scientific literature for the particular application envisioned. Of course, where the intron sequences are known, computer assisted comparisons may be carried out to identify distinct regions, and appropriate PCR primers designed accordingly.

Recombinant clones which incorporate intron DNA are readily achieved through the PCR amplification of the distinct desires region using primers, e.g., that border the region, incorporating the amplified DNA into a recombinant clone, and selecting recombinant clones which have received the intron DNA-bearing clones. The intron DNA containing clones are then purified, and, preferably, the cloned DNA sequenced sufficiently to ensure that it contains the desired sequences.

Intron DNA is then removed from the vector employed for intron DNA cloning, and employed in the construction of appropriate antisense vectors. This will entail, of course, placing the intron DNA in an antisense direction behind an appropriate promoter and positioned so as to bring the expression of the antisense intron under control of the promoter.

When selecting primers for intron sequence amplification, one will typically desire to employ primers such that at least 50 and preferably 100–200, nucleotides of the intron are amplified and thereby cloned. In general, it is believed that the larger the distinct antisense intron region is, the better able it will be to selectively down-regulate the targeted gene. Furthermore, it is believed that particular advantages will be realized through the selection of intron regions which include intron/exon boundaries, or simply just the intron side of the intron/exon boundaries. The reason for this is that RNA processing takes place at the intron/exon boundary of the RNA and it is believed that the antisense intron DNA will have its greatest effect when targeted to this junction.

The particular vector which ones employs for introduction of antisense intron coding sequences is not believed to be particularly crucial to the practice of the present invention, so long as the vector is capable of introducing the nucleic acid coding sequences into the genome of the targeted cell in a relatively stable fashion. By way of illustration, but not limitation, one can mention the following vectors, including N2A, LN, LNSX, Adenovirus and Adeno-associated virus.

The most preferred vector construct for targeting cells is the LNSX retroviral vector. This vector is based on the N2 vector, which contains the extended packaging signal that allows for the production of the vector at a high titer. This vector was modified by inserting a stop codon in place of the Pr65 gag start codon to prevent synthesis of Pr 65 gag, and by replacing the upstream region of the vector with the homologous region from Moloney murine sarcoma virus. These alterations prevent synthesis of viral proteins from the vector. Splicing is not required for efficient neo-protein expression. The neo gene is expressed from the upstream LTR promoter. An SV promoter and downstream cloning sites were added so that inserted genes such as the K-ras segment can be expressed from the internal promoter.

The following examples are included to provide actual working protocols which the inventors have developed or adopted for carrying out preferred embodiments of the invention. Those of skill in the art will readily appreciate that many of the techniques employed in the following examples are illustrative of standard laboratory practices, which have been found by the inventors to work well in the practice of the invention. It will, however, be apparent to those of skill in the art, in light of the following examples, that numerous materials and/or modifications and procedures and nevertheless achieve a useful result.

EXAMPLE I

SPECIFIC INHIBITION OF K-RAS EXPRESSION AND TUMORIGENICITY OF LUNG CANCER CELLS BY ANTISENSE RNA

A. INTRODUCTION

A wide spectrum of human cancers harbor ras genes activated by a single point mutation (Barbacid, 1987; Rodenhuis, et al., 1987; Bos, 1989; Rodenhuis, et al., 1990; Mabry, et al., 1988; Santos, et al., 1984; Taya, et al., 1984; Cline, et al., 1987; Feig, et al., 1984; Vogelstein, et al., 1988; Kumar, et al., 1990). Despite considerable knowledge of the structural aspects of the ras gene product, the functional role in physiological and pathological processes remains elusive (Barbacid, 1987). Cellular location and structural and biochemical similarities to G proteins suggest that ras gene products are involved in signal transduction (Bos, et al., 1987; Hurley, et al., 1984). The present example describes the preparation and use of an antisense RNA construct to block selectively the production of the mutated protein in the human non-small cell lung cancer (NSCLC) cell line NCI-H460A. The direct contribution of the mutated p21 protein to the malignant phenotype was also examined.

B. MATERIALS AND METHODS

H460, H322, H226, H522 non-small cell lung cancer (NSCLC) cell lines were generously provided by Drs. J. D. Minna, A. F. Gazdar, NCI Naval Medical Oncology Branch, Bethesda, Md. All cell lines were grown in regular RPMI medium, 5% FCS, in routine culture.

1. Plasmid Construction

A 2-kb genomic DNA fragment from the K-ras proto-oncogene was subcloned into an Apr-1-neo vector in both sense and antisense orientation. A 2-kb Eco RI/Pst I fragment containing second and third exon sequences together with adjoining flanking intron sequences was isolated from the SP6 vector (Oncogene Sciences) and Klenow enzyme was used to make blunt ends. Apr-1-neo vector was digested with Bam HI and blunt end ligation was performed to obtain the Apr-1-neo AS or Apr-1-neo S constructs.

2. DNA Transfections

H460a or H322a cells were electroporated with 10 $\mu$g of Apr-1-neo AS or Apr-1-neo S plasmid DNA. Forty-eight hours after transfection G418 was added into the medium at a concentration of 300 $\mu$g/ml for H460a and 200 $\mu$g/ml for H322a. Individual colonies were picked up and grown in culture for further analysis.

3. Southern Blot Analysis

High molecular weight DNA was isolated and digested with Eco R1 (Boehringer-Mannheim) (20 $\mu$g), and electrophoresed in 0.8% agarose gel, transferred onto a Gene Screen membrane (NEN) and hybridized with a $p^{32}$ nick translated 2kb genomic K-ras DNA probe.

4. Measurement of RNA Expression

Total cellular RNA was isolated from the cell lines (Chomczymsky, et al., 1987). Twenty microgram of total RNA was size fractionated in MOPS/formaldehyde gel, transferred onto a Gene Screen membrane and processed for hybridization with riboprobes. A 302 bp genomic DNA of the K-ras gene was amplified by PCR spanning the third exon and intron sequences and was subcloned into a bluescript vector. In vitro S and AS RNA probes were synthesized using either a T7 or T3 promotor.

5. Polymerase Chain Reaction

Polymerase chain reactions were performed as previously described using Taq 1 DNA polymerase (Saiki, et al., 1985). Oligonucleotide primers corresponding to region the 5' and 3' regions of codons 12 and 61 of human K-ras, H-ras, and N-ras genes were synthesized. Two micrograms of genomic DNA was subjected to 35 cycles of amplification. DNA sequences of oligonucleotide primers used for PCR amplification are listed below in Table 1.

TABLE 1

| Primers | Sequence | Target |
|---|---|---|
| KA61 | 5' TTC CTA CAG GAA GCA AGT AGT A 3' | K-ras 2nd exon |
| KB61 | 5' ACA CAA AGA AAG CCC DCC CCA 3' | |
| KA12 | 5' GAC TGA ATA TAA SCT TGT GG 3' | K-ras 1st & 2nd exon |
| KB61 | 5' ACA CAA AGA AAG CCC DCC CCA 3' | |
| HA12 | 5' GAC GGA ATA TAA GCT GGT GG 3' | H-ras 1st & 2nd exon |
| HB61 | 5' CGC ATG TAC TGG TCC CGC AT 3' | |
| NA12 | 5' GSC TGA GTA CAA ACT GGT GG 3' | N-ras 1st & 2nd exon |
| NB61 | 5' ATA CAC AGA GGA AGC CTT CG 3' | |

6. Slot Blot Oligonucleotide Hybridization

PCR amplified DNA samples (12.5, 25, 50 ng) were blotted onto a Gene Screen membrane using a slot blot apparatus (Schleicher & Schuell). The filters were prehybridized and hybridized at 55° C. in 6X SSC, 5X Denhardts and 100 µg/ml of salmon sperm DNA for 2 h. Filters were washed twice in 6X SSPE at room temperature and once for 30 mins at 58° C. Finally, blots were washed for 5 mins at 64° C. The filters were exposed to x-ray film for 12–24 h at −80° C.

7. Direct sequencing of PCR Amplified DNAs

PCR DNA corresponding to the second exon was purified in 8% polyacrylamide gel. A single DNA band was excised and purified DNA was used for asymmetric amplification in 100 µl of PCR reaction mixture. One (KA 61) amplimer was added to this mixture. After 20 cycles, single-stranded DNA was purified through gene clean (Bio 101) and DNA was eluted in 15 µl of water. Four microliters of DNA were mixed with 4 µl of 10×Taq 1 buffer and 1 µl (10 pmol) of a second amplimer (KB 61) was used as a sequencing primer and DNA was sequenced using a Sequenase kit.

8. RNA PCR Analysis cDNA synthesis was carried out in a total volume of 20 µl containing 5 Ag of total RNA and oligo (dT) as a primer (Becker-Andre, et al., 1989). A portion of the cDNA corresponding to the first and second exons was amplified to monitor the level of endogenous K-ras mRNA (FIG. 2A) using KA12 and KB61 amplimers. Denaturation, annealing, and extension were done at 92° C. for 1 min, 51° C. for 1 min and 74° C. for 1 min, respectively. However, annealing temperatures for N-ras and H-ras were 44° C. and 42° C., respectively. In addition, two amplimers were also used in the same reaction mixture to amplify a 118-bp fragment of the p53 gene as an internal control. PCR products were either transferred onto a membrane and hybridized with $^{32}P$ labelled cDNA probe or alternatively, there were directly labelled during the last cycle of amplification by adding 1 uCi of $^{32}P$ dCTP. The labelled PCR products were loaded on an 8% nondenaturing polyacrylamide gel. The gel was photographed after ethidium bromide staining, dried, and exposed to x-ray film overnight at −80° C.

9. Western Blot Analysis of RAS Protein

Protein extracts were prepared by lysing cell in TBS (10 mM TRIS ph 7.5, 100 mM Nacl, 1 mM PMSF 1% NP40, 1% deoxycholate. The extracts were cleaned by centrifugation at 10,000Xg for 1 h. The protein concentration of the supernatant was calculated spectrophotometrically. Five hundred micrograms of protein were size fractionated in 12.55% SDS polyacrylamide gel and electroblotted onto nitrocellulose membranes. Ras specific p21 protein was detected using either K-ras or pan ras specific monoclonal antibody (Oncogene Sciences) followed by $^{125}I$-labelled goat anti-mouse second antibody.

10. Tumorgenicity in Nude Mice

The tumorigenicity of these cell lines was examined by subcutaneous inoculation of $10^5$ (FIG. 3B) and $10^6$ cells in nu/nu mice. Each cell line was injected into 5 animals. Tumors were measured with linear calipers in 2 orthogonal directions by the same observer.

C. RESULTS AND DISCUSSION

Figure 1A:
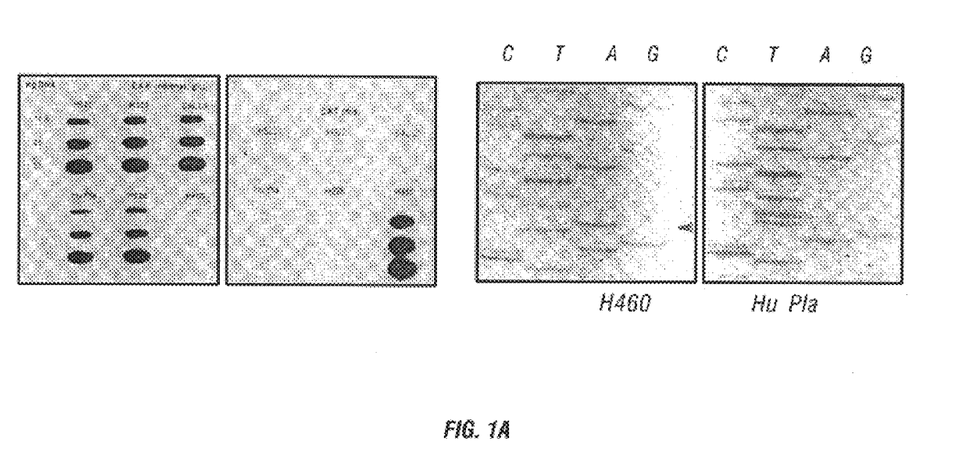
FIG. 1A) The second exon of the K-ras gene was amplified from genomic DNA of H522, H322, Calu 1, H226, H460a and human placenta by polymerase chain reaction (PCR), blotted onto a gene screen membrane and hybridized with $^{32}$P end-labeled oligonucleotide probes. FIG. A1 shows the presence of wild-type glutamine residue (CAA) at 61 codon in five cell lines except H460a. The same blot was reprobed with a histidine-specific mutated oligo probe (CAT) and only the H460a cell line PCR DNA hybridized (FIG. A2). The mutation was confirmed by direct PCR DNA sequencing. Wild-type K-ras 61 codon sequence in human placenta (FIG. A3) was compared with the H460a cell line (FIG. A4).

Segments of the K-ras gene containing first and second exons were amplified from a number of NSCLC cell line DNAs by polymerase chain reaction (Saiki, et al, 1985) and subsequently hybridized with a set of $^{32}P$-labelled oligonucleotide probes (FIGS. 1A-1 & 2). Mutations were confirmed by a direct PCR DNA sequencing method. A homozygous mutation at codon 61 was detected in the NCI-H460A large cell undifferentiated NSCLC cell line with a normal glutamine residue (CAA) substituted by histidine (CAT). This cell line is highly tumorigenic in nude mice.

Figure 1B:
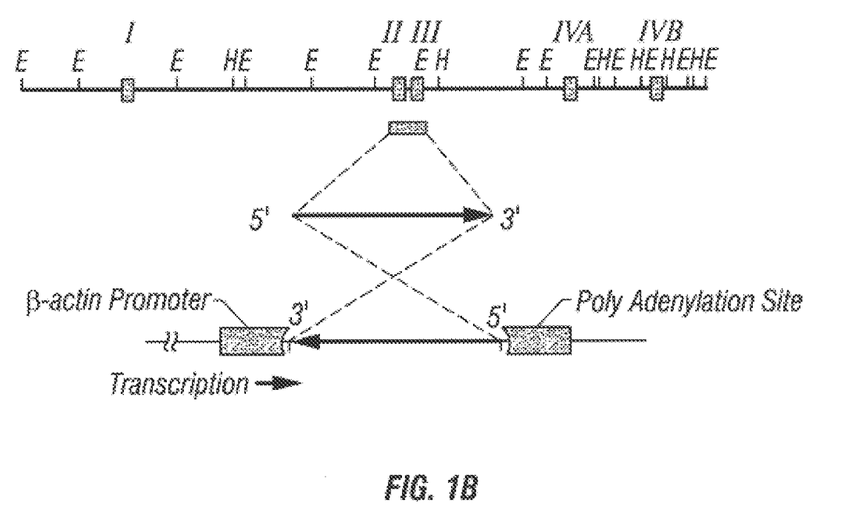
Figure 1C:
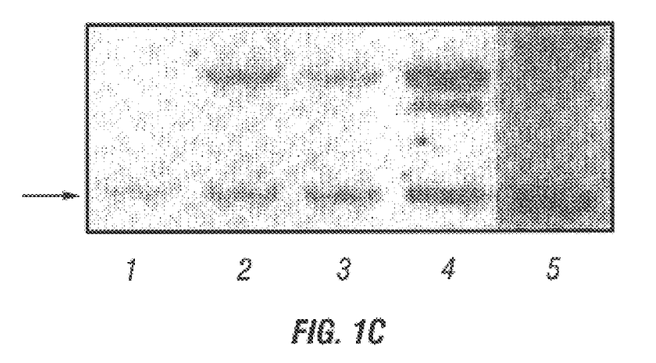
Figure 1D:
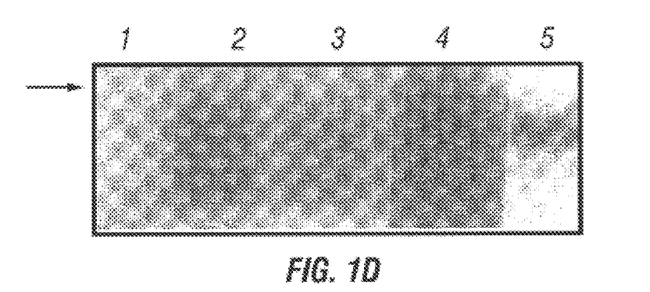

A recombinant plasmid clone was constructed using a wild-type 2 kb K-ras genomic DNA segment carrying second and third exons together with flanking intron sequences subcloned into an Apr-1-neo expression vector (Gunning, et al., 1984) in the antisense orientation (AS; FIG. 1G). Sense orientation (S) plasmid constructs were used as a control (FIG. 1B). AS or S K-ras RNA synthesis was accomplished by transfecting H460a cells, a cloned derivative of the NCI-H460A cell line, with Apr-1-neo AS or Apr-1-neo S constructs by electroporation. The β-actin promoter of the vector was constitutively capable of directing the synthesis of RNA from the inserted DNA. The Apr-1-neo vector offered suitable G418 marker gene expression for selection of the transfectants.

Individual G418 resistant colonies were selected and grown in culture for further analysis. Stable integration of the plasmid DNA in the transfectants was examined by Southern hybridization with a 2 kb DNA insert from the original plasmid clone as a probe (FIG. 1C). The southern blot analysis showed a single 3 kb Eco RI band corresponding to the endogenous K-ras gene in the parental H460a cell line, but additional bands were observed in the individual clones indicating single or multiple copy inserts.

The extent of stable AS RNA expression and its effect on the endogenous K-ras mRNA level was investigated. Total RNA was extracted from subconfluent, growing cultures (Gunning, et al., 1987). The presence of AS and S RNA was detected by northern blot hybridization using either an S or AS RNA probe synthesized in vitro from a Bluescript vector carrying a 302 bp K-ras DNA insert corresponding to the third exon and part of the intron sequences (FIG. 1D). Interestingly, the clones carrying the Apr-1-neo AS vector show one RNA band at about 1.5 kb, but the cells carrying the S construct show two RNA species. The reason for this is unknown, but the possibility exists that the RNA synthesized from the genomic DNA under control of the β-actin promoter could be processed in vivo. However, no corresponding hybridization band was detected in H460a cells, which indicated a significantly higher level of K-ras RNA was synthesized under the β-actin promoter.

Figure 1E:
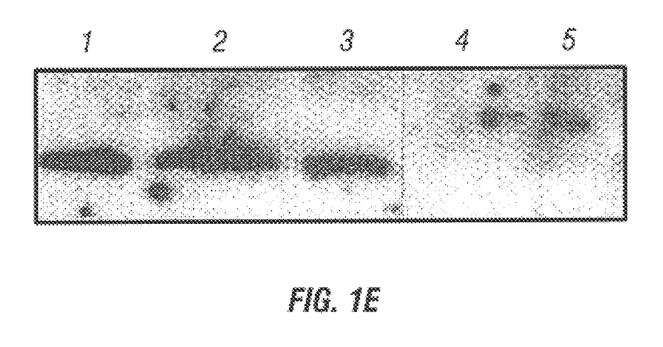
Figure 1F:
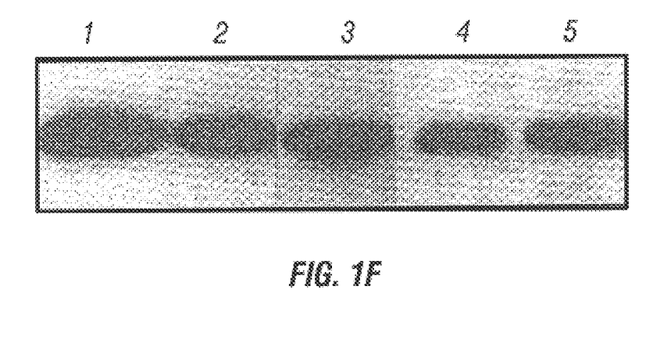
Figure 1G:
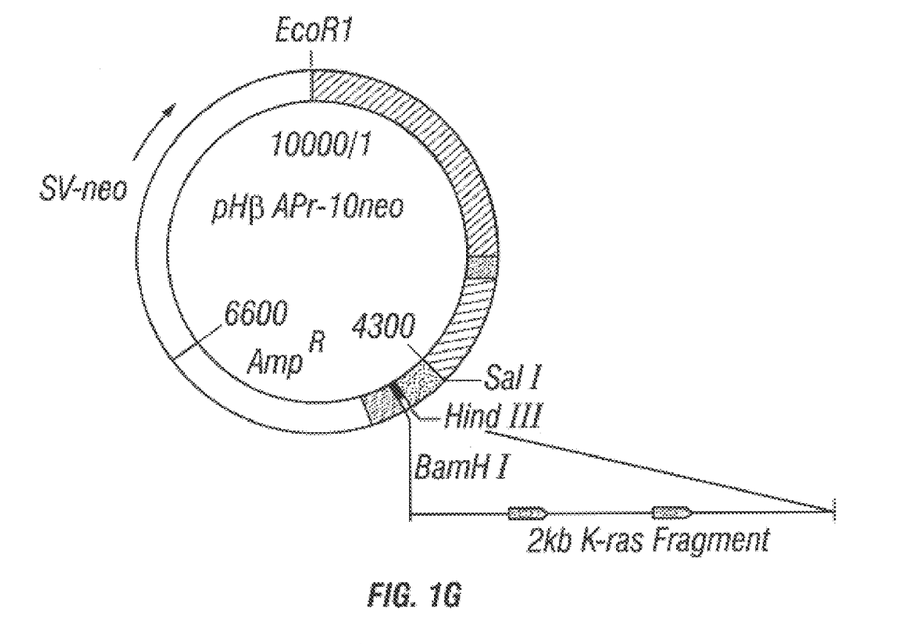

Next, the p21 protein level in these transfectants was analyzed by western blot analysis (FIGS. 1E, F). A K-ras-specific p21 monoclonal antibody (oncogene Science) was used to determine the level of K-ras protein in transfectants, parental H460a cells, and Calu-1 cells, which have a high level of K-ras gene expression (FIG. 1E). Western blot analysis showed a 95% reduction in K-ras p21 protein synthesis in the clones expressing the AS RNA, while parental cells, S K-ras clones, and Calu-1 cells showed a significant level of K-ras p21 protein. These results indicate that AS RNA can effectively block the synthesis of K-ras specific protein. Since members of the ras gene family share a great deal of sequence homology and code for a similar p21 ras protein, we examined the total ras protein product in these clones was examined using a PAN ras monoclonal antibody (New England Nuclear) to determine whether a reduced level of K-ras protein reflects any change in H-ras and N-ras p21 protein synthesis (FIG. 1F). Western blot analysis revealed only a slight decrease in overall ras protein level in all clones containing Apr-1-neo-AS, as compared to 460a parental cells.

Figure 2A:
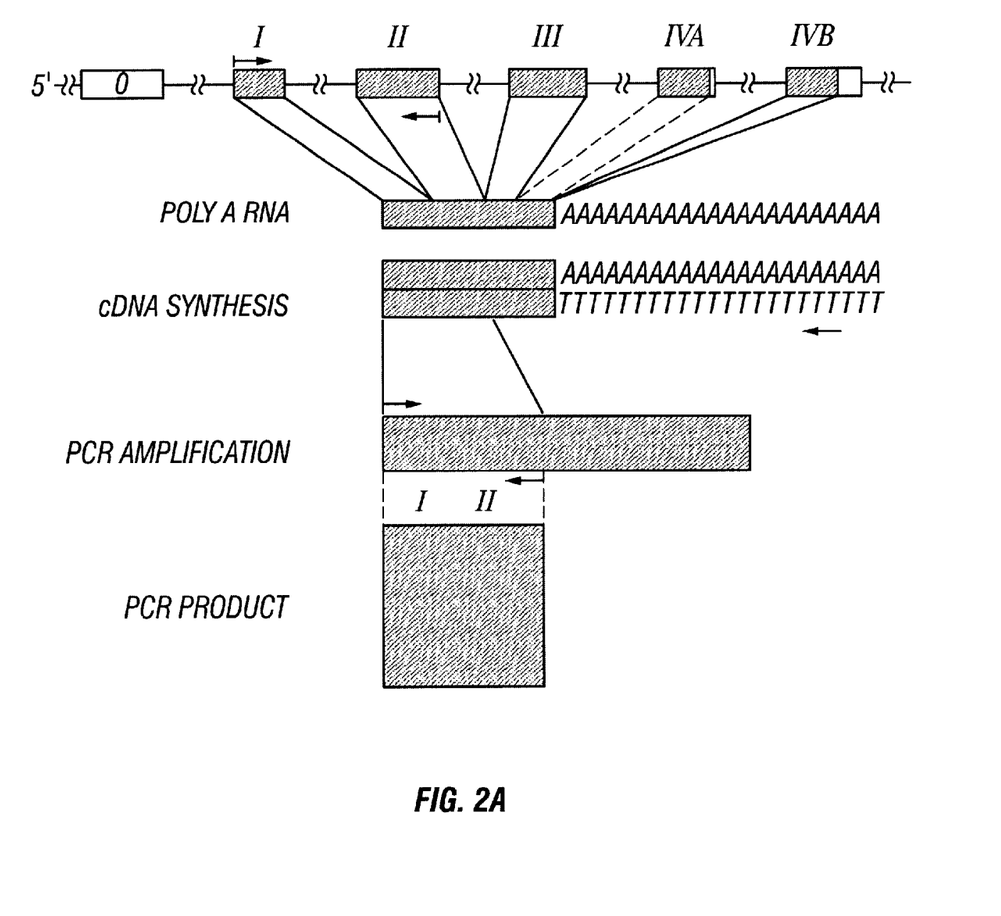

The effect of AS RNA on the specific production of mature endogenous K-ras mRNA was analyzed by cDNA PCR (FIG. 2). cDNA synthesized from the total RNA (Chomczymsky, et al., 1987) was subjected to PCR amplification using amplimers corresponding to the 5'-end of the first exon and the 3'-end of the second exon (FIG. 2A). Because the AS RNA was generated only from a second and third exon of the K-ras gene, PCR amplified cDNA represented the level of endogenous K-ras mRNA. A 246-bp amplified DNA fragment was labelled by $^{32}$P dCTP and subsequently analyzed by polyacrylamide gel electrophoresis. In addition, a 118-bp segment of endogenous p53 cDNA was co-amplified in the same reaction mixture using p53 specific amplimers to serve as an internal control for the PCR.

Figure 2B:
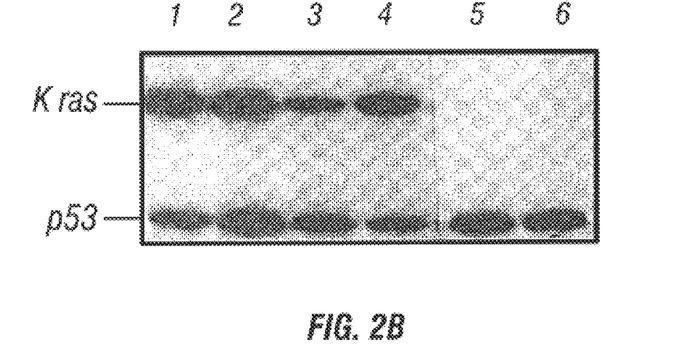
Figure 2C:
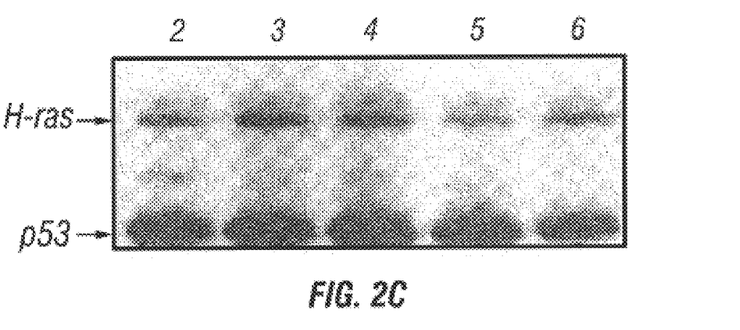
Figure 2D:
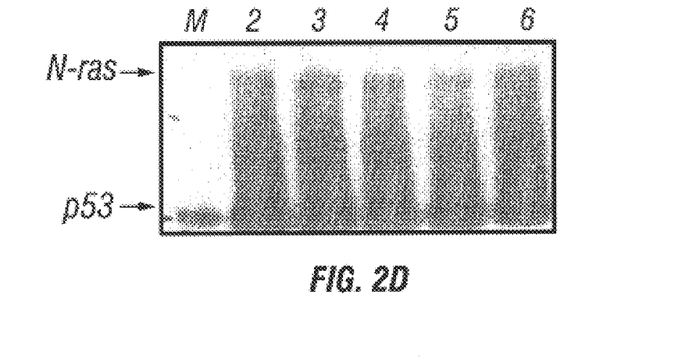

Results showed that H460a cells, clones expressing S RNA, and the Calu-1 cell line expressed K-ras mRNA, as evidenced by the presence of a high level of amplification of the 246-bp cDNA product (FIG. 2B). H460a clones expressing AS RNA showed very little amplification, and cellular K-ras mRNA synthesis appeared to be completely inhibited (FIG. 2B, lanes 5 and 6). In contrast, the endogenous p53 expression remained unaffected. This prompted us to investigate the level of expression for other ras genes in these clones. We employed the same cDNA PCR methodology to analyze the N-ras and H-ras mRNA level using N-ras and H-ras-specific oligonucleotides as amplimers. A steady state level of H-ras and N-ras gene expression was observed, but no obvious change either in Apr-1-neo AS or Apr-1-neo S transfectants was noticed (FIGS. 2C, D). The p53 gene expression serving as a control in these experiments remained unaffected. Thus, inhibition of K-ras expression by our AS RNA construct is specific.

Figure 3A:
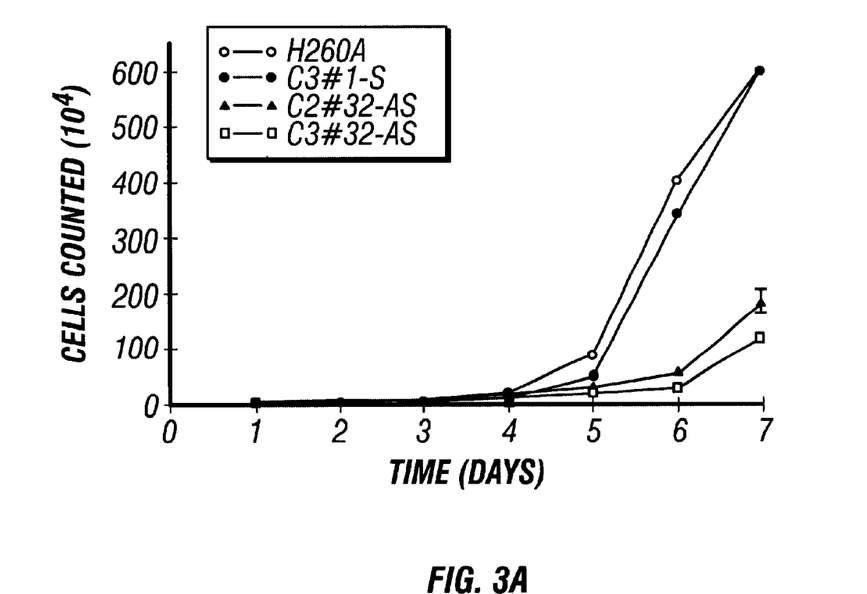

H460a clones expressing AS K-ras RNA continued to grow in culture. However, H460a Apr-1-neo AS transfectants showed a three-fold reduction in growth, compared to the H460a Apr-1-neo-S transfectants and the parental H460a cells (FIG. 3A). The H322 NSCLC cell lung cancer cell line has wild-type ras family genes. H322 Apr-1-neo AS and Apr-1-neo S transfectants had identical growth characteristics, indicating that inhibition of wild-type K-ras is not sufficient to alter tumor cell growth rate. These results together indicate that the presence of sense K-ras RNA did not alter the growth kinetics of H460a cells. However, the marked growth retardation of the K-ras Apr-1-neo-AS transfectants suggests that the mutated p21 protein contributes to the faster growth rate of these cells.

Figure 3B:
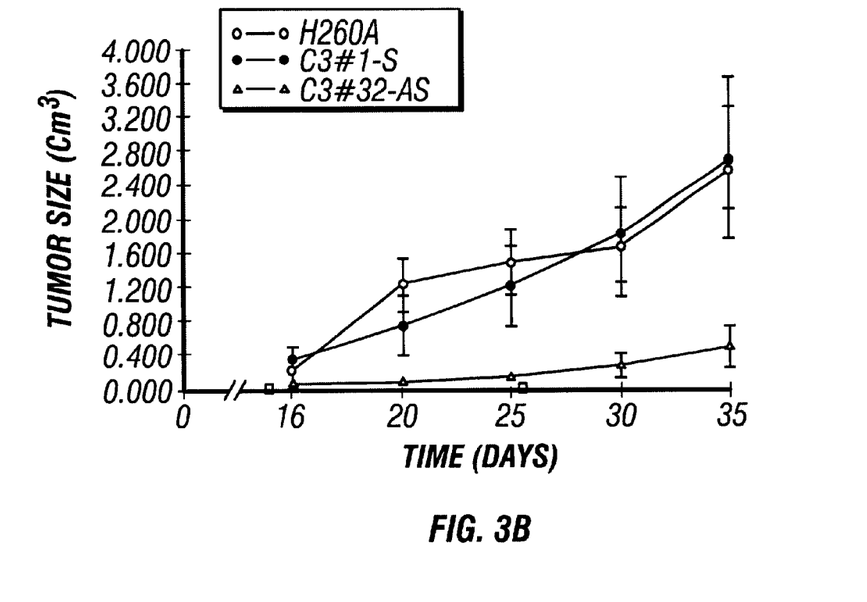

The tumorigenicity of cell lines expressing AS RNA was assessed by subcutaneous injection of $10^5$ and $10^6$ cells in nu/nu mice. Subcutaneous inoculation of H460a cells at both doses led to the formation of tumors in 15 days in all mice (3 to 5 mice per group in 3 separate experiments). No tumor developed in mice injected with $10^5$ cells for both clones of H460a AS cells during 120 days of observation in a total of ten mice, whereas all mice receiving H460a cells developed tumors. When the inoculum was increased to $10^6$ cells, tumors grew in all mice, but the tumors in mice receiving AS clones grew at a slower rate than H460a cells or the S control (FIG. 3B). Tumors were excised and analyzed for K-ras expression by cDNA-PCR. K-ras expression was not detected in tumors arising from injection of AS clones but was present in S clones and H460a tumors.

The above experiments indicate that in H460a cells engineered to synthesize AS K-ras RNA, the level of K-ras mRNA and K-ras p21 protein are effectively down regulated. Reduction in the expression of K-ras mutated gene reproducibly reduced the rate of tumor growth in nu/nu mice. Our studies show that a construct can be made that distinguishes among members of the ras family. Previous studies with AS oligonucleotides showed inhibition of p21 expression which led to cell death (Brown, et al., 1989; Debus, et al., 1990). Our data indicate that AS RNA generated from the genomic DNA of the K-ras gene can specifically inhibit K-ras expression. In our model inhibition of activated K-ras reduced the growth rate of the H460a cells. However, there was no effect on cell viability or continued growth in culture. This suggests that redundancy in p21 expression may compensate for absence of expression by one member of this family so that functions essential for maintenance of cell viability are preserved. However, tumorigenicity was maintained in the absence of activated K-ras expression although the rate of tumor growth was diminished. We hypothesize that in human NSCLC, ras mutations confer a growth advantage to the malignant cell.

The present invention has been disclosed in terms of preferred modes found to work well in the practice of the invention. However, numerous modifications and changes in the steps, procedures used and material will become apparent to those of skill in the art in light of the disclosure. All such modifications are intended to be within the spirit of the present invention and scope of the appended claims.

REFERENCES

The following references are hereby incorporated by reference to the extent that they describe, explain, teach methodology for or provide useful materials or compositions for use in connection with the practice of the present invention, for the reasons specified in the foregoing text.

Barbacid, et al. (1987), *Genes. Ann. Rev. Biochem.*, 56:779.
Becker-Andre, et al. (1989), *Nucleic Acids Res.*, 17 (22):947.
Bishop (1987), *Science*, 235:305–311.
Bos (1989), *Cancer Res.*, 49 4682–4689.
Bos, et al. (1987), *Nature*, 327:293–297.
Bos (1989), *Cancer Res.*, 49:4682–4689.
Brown, et al. (1989), *Oncogene Research*, 4:243–252.
Brown, et al. (1989), *Oncogene Res.*, 4:243–252.
Buvoli, et al. (1983), *Nature*:304:497–500.
Chomczymsky, et al. (1987), *Anal. Biochem.*, 162:156–159.
Cline, et al. (1987), *Cancer*, 60:2669–2674.
Cooper (1982), *Science*, 218:801–806.
Debus, et al. (1990), *J. Cancer Res. Clin. Oncol.*, 116 (Suppl., Part 1) S-162.
Delauney, et al. (1988), *Proc. Natl. Acad. Sci. USA*, 85:4300–4304.
Der, et al. (1982), *Proc. Natl. Acad. Sci. USA*, 79:3637–3640.
Ellis, et al., (1981), *Nature*, 292:506–511.
Feig, et al. (1984), *Science*, 223:698–701.
Gunning, et al. (1987), *Proc. Natl. Acad. Sci. USA*, 84 (14):4831–4835.
Hamtzoponlos, et al. (1989), *Proc. Natl. Acad. Sci. U.S.A.*, 86:3519.
Hurley, et al. (1984), *Science*, 226:860–862.
Kasid, et al. (1989), *Science*, 243:1354–1356.
Khokha, et al. (1989), *Science*, 243:957–960.
Krontiris, et al. (1981), *Proc. Natl. Acad. Sci. USA*, 78:1181–1184.
Kumar, et al. (1990), *Science*, 248:1101–1104.
Lane, et al. (1982), *Cell*, 28:873–880.
Mabry, et al. (1988), *Proc. Natl. Acad. Sci. USA*, 85:6523–6527.
Miller, et al. (1989), *Biotech.*, 7:980
Murray, et al. (1981), *Cell*, 25:355–361.
Papageorge, et al. (1982), *J. Virol.*, 44:509–519.
Parada, et al. (1982), *Nature*, 297:474–478.
Perucho, et al. (1981), *Cell*, 27:467–476.
Prochownik, et al. (1988), *Mol. Cell. Biol.*, 8:3683–3695.
Pulciani, et al. (1982), *Proc. Natl. Acad. Sci. USA*, 79:2845–2849.
Pulciani, et al. (1982), *Nature*, 300:539–542.
Pulciani et al. (1982), *Proc. Natl. Acad. Sci. USA*, 79:2845–2849.
Rodenhuis, et al. (1987), *N. Engl. J. Med.*, 317;15:929–935.
Rodenhuis, et al. (1990), *Proc. Amer. Soc. Clin. Oncol.*, 9:228.
Saiki, et al. (1985), *Science*, 230:1350–1354.
Santos, et al. (1982), *Nature*, 298:343–347.
Santos, et al. (1984), *Science*, 223:661–664.
Shimizu, et al. (1983), *Proc. Natl. Acad. Sci. USA*, 80:2112–2116.
Shimizu, et al. (1983), *Proc. Natl. Acad. Sci. USA*, 80:383–387.
Smith, et al. (1986), *Proc. Natl. Acad. Sci. USA*, 83:2787–2791.
Spandidos, et al. (1989), *J. Pathol.*, 157:1–10.
Tabin, et al. (1982), *Nature*, 300:143–149.
Taparowski, et al. (1982), *Nature*, 300:762–765.
Taya, et al. (1984), *EMBO. J.*, 3:2943–2946.
Travali, et al. (1990), *FASEB*, 4:3209–3214.
Vogelstein, et al. (1988), *N. Engl. J. Med.*, 319:525–532.
Wickstrom, et al. (1988), *Proc. Natl. Acad. Sci. USA*, 85:1028–1032.
Yamamoto, et al. (1985), *Prog. Med. Virol.*, 32:101–114.
Yuasa, et al. (1983), *Nature*, 303:775–779.

What is claimed is:

1. A nucleic acid molecule which selectively inhibits the expression of the p21 K-ras oncogene, the nucleic acid molecule encoding an antisense RNA molecule comprising sequences complementary to exons II and III and intron II of the p21 K-ras oncogene, the antisense coding region of the nucleic acid molecule being positioned under the control of the β-actin promoter.

2. The nucleic acid molecule of claim 1, further defined as a DNA molecule.

3. The nucleic acid molecule of claim 1, further defined as a vector.

4. The nucleic acid molecule of claim 3, further defined as a plasmid.

5. The nucleic acid molecule of claim 3, further defined as a retrovirus.

6. An antisense RNA molecule which selectively inhibits the expression of the p21 K-ras oncogene, the antisense RNA molecule comprising sequences complementary to exons II and III and intron II of the p21 K-ras oncogene.

7. A DNA molecule capable of expressing an antisense RNA molecule in accordance with claim 6.

* * * * *